US008188223B2

(12) United States Patent
Beirnaert et al.

(10) Patent No.: US 8,188,223 B2
(45) Date of Patent: *May 29, 2012

(54) SERUM ALBUMIN BINDING PROTEINS

(75) Inventors: Els Beirnaert, Bellem (BE); Hilde Adi Pierrette Revets, Meise (BE); Hendricus Renerus Jacobus Mattheus Hoogenboom, Maastricht (NL)

(73) Assignee: Ablynx N.V., Zwijnaarde (BE)

( * ) Notice: Subject to any disclaimer, the term of this patent is extended or adjusted under 35 U.S.C. 154(b) by 1230 days.

This patent is subject to a terminal disclaimer.

(21) Appl. No.: 11/587,749

(22) PCT Filed: May 17, 2006

(86) PCT No.: PCT/EP2006/004679
§ 371 (c)(1),
(2), (4) Date: Oct. 27, 2006

(87) PCT Pub. No.: WO2006/122787
PCT Pub. Date: Nov. 23, 2006

(65) Prior Publication Data
US 2009/0028880 A1    Jan. 29, 2009

Related U.S. Application Data

(60) Provisional application No. 60/682,332, filed on May 18, 2005.

(51) Int. Cl.
A61K 39/395     (2006.01)
C07K 16/46      (2006.01)
(52) U.S. Cl. .............. 530/350; 530/387.1; 530/387.3; 424/134.1
(58) Field of Classification Search .............. None
See application file for complete search history.

(56) References Cited

U.S. PATENT DOCUMENTS

| | | |
|---|---|---|
| 5,530,101 A | 6/1996 | Queen et al. |
| 6,262,238 B1 | 7/2001 | Steipe et al. |
| 6,670,453 B2 | 12/2003 | Frenken et al. |
| 7,084,257 B2 | 8/2006 | Deshpande et al. |
| 7,368,111 B2 | 5/2008 | Thompson et al. |
| 7,432,238 B2 | 10/2008 | Kisiel et al. |
| 8,097,251 B2 | 1/2012 | Muyldermans et al. |
| 2002/0001587 A1 | 1/2002 | Erickson et al. |
| 2002/0165387 A1 | 11/2002 | Kerr Anderson et al. |
| 2003/0129659 A1 | 7/2003 | Whelihan et al. |
| 2004/0071705 A1 | 4/2004 | Sato et al. |
| 2005/0054001 A1 | 3/2005 | Muyldermans |
| 2005/0271663 A1 | 12/2005 | Ignatovich et al. |
| 2006/0034845 A1 | 2/2006 | Silence et al. |
| 2006/0106203 A1 | 5/2006 | Winter et al. |
| 2006/0228355 A1 | 10/2006 | Laeremans et al. |
| 2007/0031424 A1 | 2/2007 | Muyldermans |
| 2007/0077249 A1 | 4/2007 | Silence et al. |
| 2007/0178082 A1 | 8/2007 | Silence et al. |
| 2007/0237769 A1 | 10/2007 | Silence et al. |
| 2007/0269422 A1 | 11/2007 | Beirnaert et al. |
| 2008/0008713 A1 | 1/2008 | Brewis |
| 2009/0022721 A1 | 1/2009 | Silence et al. |
| 2009/0028880 A1 | 1/2009 | Beirnaert et al. |
| 2010/0047241 A1 | 2/2010 | Muyldermans |
| 2010/0297111 A1 | 11/2010 | Beirnaert |
| 2011/0251373 A1 | 10/2011 | Muyldermans |

FOREIGN PATENT DOCUMENTS

| | | |
|---|---|---|
| EP | 93201239.6 | 4/1993 |
| EP | 0 584 421 A1 | 3/1994 |
| EP | 98300525.7 | 1/1998 |
| EP | 1 399 484 | 6/2001 |
| GB | 0115841.9 | 6/2001 |
| JP | 6-2175426 A | 8/1987 |
| JP | 6-502526 | 3/1994 |
| WO | WO 92/01787 A1 | 2/1992 |
| WO | WO 94/04678 A1 | 3/1994 |
| WO | WO 94/13804 A1 | 6/1994 |
| WO | WO 94/25591 A1 | 11/1994 |
| WO | WO 99/20749 A2 | 4/1999 |
| WO | WO 99/37681 A2 | 7/1999 |
| WO | WO 99/42077 A2 | 8/1999 |
| WO | WO 00/09757 A1 | 2/2000 |
| WO | WO 00/73430 A2 | 12/2000 |
| WO | WO 01/44301 A1 | 6/2001 |
| WO | WO 01/45746 A2 | 6/2001 |
| WO | WO 01/90190 A2 | 11/2001 |
| WO | WO 02/48193 A2 | 6/2002 |
| WO | WO 03/002609 A2 | 1/2003 |
| WO | WO 03/035694 A2 | 5/2003 |
| WO | WO 2004/001064 A2 | 12/2003 |

(Continued)

OTHER PUBLICATIONS

Janeway et al. Immunobiology, 3rd Ed. Garland Press, 1997, p. 3:7-3:11.*
Fundamental Immunology, William E. Paul, MD 3rd ed. 1993, p. 242.*
Portolano et al., J. Immunology, 1993, vol. 150. p. 880-887.*
Carter et al., "Structure of Serum Albumin," *Advances in Protein Chemistry* 1994; 45: 153-203.
Chavez et al., "Antibody as an Immunological Probe for Studying the Refolding of Bovine Serum Albumin. An Immunochemical Approach to the Identification of Possible Nucleation Sites," *The Journal of Biological Chemistry* 1978; 253(22): 8081-8086.
Dennis et al., "Albumin Binding as a General Strategy for Improving the Pharmacokinetics of Proteins," *The Journal of Biological Chemistry* 2002; 277(38): 35035-35043.

(Continued)

*Primary Examiner* — Yunsoo Kim
(74) *Attorney, Agent, or Firm* — Wolf, Greenfield & Sacks, P.C.

(57) ABSTRACT

The present invention relates to amino acid sequences that are capable of binding to serum albumin, which sequences do not significantly reduce or inhibit the binding of serum albumin to FcRn or significantly reduce the half-life of serum albumin. It further relates to proteins and polypeptides comprising or essentially consisting of such amino acid sequences; to nucleic acids that encode such amino acid sequences, proteins or polypeptides; to compositions, and in particular pharmaceutical compositions, that comprise such amino acid sequences, proteins and polypeptides; and to uses of such amino acid sequences, proteins and polypeptides.

18 Claims, No Drawings

FOREIGN PATENT DOCUMENTS

| | | |
|---|---|---|
| WO | WO 2004/003019 A2 | 1/2004 |
| WO | WO 2004/003019 A3 | 1/2004 |
| WO | WO 2004/041862 A2 | 5/2004 |
| WO | WO 2005/035572 A2 | 4/2005 |
| WO | WO 2006/038027 A2 | 4/2006 |
| WO | WO 2006/059106 A2 | 6/2006 |
| WO | WO 2007/049017 A2 | 5/2007 |
| WO | WO 2008/149144 A2 | 12/2008 |
| WO | WO 2008/149146 A2 | 12/2008 |
| WO | WO 2008/149147 A2 | 12/2008 |
| WO | WO 2008/149148 A2 | 12/2008 |
| WO | WO 2009/068627 A2 | 6/2009 |

OTHER PUBLICATIONS

Ferguson et al., "Immunoregulatory Properties of Antigenic Fragments from Bovine Serum Albumin," *Cellular Immunology* 1983; 78(1): 1-12.
Wunder et al., "Albumin-Based Drug Delivery as Novel Therapeutic Approach for Rheumatoid Arthritis," *The Journal of Immunology* 2003; 170(9): 4793-4801.
U.S. Appl. No. 60/207,234, Jasmid Tanha et al.
Ameloot et al., Heterotrimers formed by tumor necrosis factors of different species or muteins. J Biol Chem. Jul. 20, 2001;276(29):27098-103. Epub May 22, 2001.
Anker et al., $V_H$ and $V_L$ region structure of antibodies that recognize the (NANP)3 dodecapeptide sequence in the circtunsporozoite protein of Plasmodium falciparum. Eur J Immunol. Dec. 1990;20(12):2757-61.
Arbabi Ghahroudi et al., Selection and identification of single domain antibody fragments from camel heavy-chain antibodies. FEBS Lett. Sep. 15, 1997;414(3):521-6.
Babu et al., Omalizumab, a novel anti-IgE therapy in allergic disorders. Expert Opin Biol Ther. Nov. 2001;1(6):1049-58.
Black et al., Development of hydrophobicity parameters to analyze proteins which bear post-pr cotranslational modifications. Anal Biochem. Feb. 15, 1991;193(1):72-82.
Bødtger et al., The safety and efficacy of subcutaneous birch pollen immunotherapy—a one-year, randomized, double-blind, placebo-controlled study. Allergy. Apr. 2002;57(4):297-305.
Brorson et al., Mutational analysis of avidity and fine specificity of anti-levan antibodies. J Immunol. Dec. 15, 1999;163(12):6694-701.
Brummell et al., Probing the combining site of an anti-carbohydrate antibody by saturation-mutagenesis: role of the heavy-chain CDR3 residues. Biochemistry. Feb. 2, 1993;32(4):1180-7. Abstract only.
Burks et al., In vitro scanning saturation mutagenesis of an antibody binding pocket. Proc Natl Acad Sci U S A. Jan. 21, 1997;94(2):412-7.
Caldas et al., Humanization of the anti-CD18 antibody 6.7: an unexpected effect of a framework residue in binding to antigen. Mol Immunol. May 2003;39(15):941-52.
Casset et al., A peptide mimetic of an anti-CD4 monoclonal antibody by rational design. Biochem Biophys Res Commun. Jul. 18, 2003;307(1):198-205.
Chen et al., Selection and analysis of an optimized anti-VEGF antibody: crystal structure of an affinity-matured Fab in complex with antigen. J Mol Biol. Nov. 5, 1999;293(4):865-81.
Chien et al., Significant structural and functional change of an antigen-binding site by a distant amino acid substitution: proposal of a structural mechanism. Proc Natl Acad Sci U S A. Jul. 1989;86(14):5532-6.
Chothia et al., Domain association in immunoglobulin molecules. The packing of variable domains. J Mol Biol. Dec. 5, 1985;186(3):651-63.
Chukwuocha et al., Isolation, characterization and sequence analysis of five IgG monoclonal anti-beta 2-glycoprotein-1 and anti-prothrombin antigen-binding fragments generated by phage display. J Immunol. Oct. 15, 1999;163(8):4604-11.
Colman, Effects of amino acid sequence changes on antibody-antigen interactions. Res in Immunol. 1994;145:33-36.
Conrath et al., Antigen binding and solubility effects upon the veneering of a camel VHH in framework-2 to mimic a VH. J Mol Biol. Jul. 1, 2005;350(1):112-25.
Conrath et al., Beta-lactamase inhibitors derived from single-domain antibody fragments elicited in the camelidae. Antimicrob Agents Chemother. Oct. 2001;45(10):2807-12.
Conrath et al., Camel single-domain antibodies as modular building units in bispecific and bivalent antibody constructs. J Biol Chem. Mar. 9, 2001;276(10):7346-50. Epub Oct. 25, 2000.
Coppieters et al., Formatted anti-TNF-alpha nanobodies show superior efficacy in a collagen-induced arthritis model in mice. Arthritis Rheum. Sep. 2005;52(9):Supp. S362-3.
Coppieters et al., Formatted anti-tumor necrosis factor alpha VHH proteins derived from camelids show superior potency and targeting to inflamed joints in a murine model of collagen-induced arthritis. Arthritis Rheum. Jun. 2006;54(6):1856-66.
Cortez-Retamozo et al., Efficient cancer therapy with a nanobody-based conjugate. Cancer Res. Apr. 15, 2004;64(8):2853-7.
Davies and Riechmann, Single antibody domains as small recognition units: design and in vitro antigen selection of camelized, human VH domains with improved protein stability. Protein Eng. Jun. 1996;9(6):531-7.
De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.
Desmyter et al., Antigen specificity and high affinity binding provided by one single loop of a camel single-domain antibody. J Biol Chem. Jul. 13, 2001;276(28):26285-90. Epub May 7, 2001.
Desmyter et al., Crystal structure of a camel single-domain VH antibody fragment in complex with lysozyme. Nat Struct Biol. Sep. 1996;3(9):803-11.
Dimasi et al., Characterization of engineered hepatitis C virus NS3 protease inhibitors affinity selected from human pancreatic secretory trypsin inhibitor and minibody repertoires. J Virol. Oct. 1997;71(10):7461-9.
Dufner et al., Harnessing phage and ribosome display for antibody optimisation. Trends Biotechnol. Nov. 2006;24(11):523-9. Epub Sep. 26, 2006.
Dumoulin et al., Single-domain antibody fragments with high conformational stability. Protein Sci. Mar. 2002;11(3):500-15.
Fan et al., Three-dimensional structure of an Fv from a human IgM immunoglobulin. J Mol Biol. Nov. 5, 1992;228(1):188-207.
Giusti et al., Somatic diversification of S107 from an antiphosphocholine to an anti-DNA autoantibody is due to a single base change in its heavy chain variable region. Proc Natl Acad Sci U S A. May 1987;84(9):2926-30.
Gordon et al., A pilot study of treatment of active ulcerative colitis with natalizumab, a humanized monoclonal antibody to alpha-4 integrin. Aliment Pharmacol Ther. Apr. 2002;16(4):699-705.
Hamers-Casterman et al., Naturally occurring antibodies devoid of light chains. Nature. Jun. 3, 1993;363(6428):446-8.
Harmsen et al., Llama heavy-chain V regions consist of at least four distinct subfamilies revealing novel sequence features. Mol Immunol. Aug. 2000;37(10):579-90.
Harmsen et al., Properties, production, and applications of camelid single-domain antibody fragments. Appl Microbiol Biotechnol. Nov. 2007;77(1):13-22. Epub Aug. 18, 2007.
Holm et al., Functional mapping and single chain construction of the anti-cytokeratin 8 monoclonal antibody TS1. Mol Immunol. Feb. 2007;44(6):1075-84. Epub Sep. 20, 2006.
Hommes et al., Infliximab treatment for Crohn's disease: one-year experience in a Dutch academic hospital. Inflamm Bowel Dis. Mar. 2002;8(2):81-6.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Jang et al., The structural basis for DNA binding by an anti-DNA autoantibody. Mol Immunol. Dec. 1998;35(18):1207-17.
Klooster et al., Improved anti-IgG and HAS affinity ligands: clinical application of VHH antibody technology. J Immunol Methods. Jul. 31, 2007;324(1-2):1-12. Epub May 11, 2007.
Kobayashi et al., Tryptophan H33 plays an important role in pyrimidine (6-4) pyrimidone photoproduct binding by a high-affinity antibody. Protein Eng. Oct. 1999;12(10):879-84.

Kumar et al., Molecular cloning and expression of the Fabs of human autoantibodies in *Escherichia coli*. Determination of the heavy or light chain contribution to the anti-DNA/-cardiolipin activity of the Fab. J Biol Chem. Nov. 10, 2000;275(45):35129-36.

Lauwereys et al., Potent enzyme inhibitors derived from dromedary heavy-chain antibodies. EMBO J. Jul. 1, 1998;17(13):3512-20.

López-Requena et al., Gangliosides, Ab1 and Ab2 antibodies II. Light versus heavy chain: An idiotype-anti-idiotype case study. Mol Immunol. Feb. 2007;44(5):1015-28. Epub Apr. 18, 2006.

MacCallum et al., Antibody-antigen interactions: contact analysis and binding site topography. J Mol Biol. Oct. 11, 1996;262(5):732-45.

Mariuzza et al., The structural basis of antigen-antibody recognition. Annu Rev Biophys Biophys Chem. 1987;16:139-59. Review.

Muyldermans et al., Recognition of antigens by single-domain antibody fragments: the superfluous luxury of paired domains. Trends Biochem Sci. Apr. 2001;26(4):230-5.

Muyldermans et al., Unique single-domain antigen binding fragments derived from naturally occurring camel heavy-chain antibodies. J Mol Recognit. Mar.-Apr. 1999;12(2):131-40.

Muyldermans, Single domain camel antibodies: current status. J Biotechnol. Jun. 2001;74(4):277-302.

Nargessi et al., Solid-phase fluoroimmunoassay of human albumin in biological fluids. Clin Chim Acta. Nov. 1, 1978;89(3):455-60.

Nguyen et al., Camel heavy-chain antibodies: diverse germline V(H)H and specific mechanisms enlarge the antigen-binding repertoire. EMBO J. Mar. 1, 2000;19(5):921-30.

Nguyen, Thesis, Generation of heavy chain antibodies in camelids. Free University of Brussels, Faculty of Science, Inst. For Molecular Biology and Biotechnology, Lab. of Ultrastructure, (Submitted Aug. 2001).

Nuttall et al., Immunoglobulin VH domains and beyond: design and selection of single-domain binding and targeting reagents. Curr Pharm Biotechnol. Nov. 2000;1(3):253-63.

Pessi et al., A designed metal-binding protein with a novel fold. Nature. Mar. 25, 1993;362(6418):367-9.

Quiocho, Protein engineering. Making of the minibody. Nature. Mar. 25, 1993;362(6418):293-4.

Rahbarizadeh et al., Production of novel recombinant single-domain antibodies against tandem repeat region of MUC1 mucin. Hybrid Hybridomics. Jun. 2004;23(3):151-9.

Reiter et al., An antibody single-domain phage display library of a native heavy chain variable region: isolation of functional single-domain VH molecules with a unique interface. J Mol Biol. Jul. 16, 1999;290(3):685-98.

Riechmann et al., Single domain antibodies: comparison of camel VH and camelised human VH domains. J Immunol Methods. Dec. 10, 1999;231(1-2):25-38.

Riechmann, Rearrangement of the former VL interface in the solution structure of a camelised, single antibody VH domain. J Mol Biol. Jun. 28, 1996;259(5):957-69.

Rudikoff et al., Single amino acid substitution altering antigen-binding specificity. Proc Natl Acad Sci U S A. Mar. 1982;79(6):1979-83.

Sheikh et al., Enhanced recognition of reactive oxygen species damaged human serum albumin by circulating systemic lupus erythematosus autoantibodies. Autoimmunity. Nov. 2007;40(7):512-20.

Shimamoto et al., Inhibition of Helicobacter pylori infection by orally administered yolk-derived anti-Helicobacter pylori antibody. Hepatogastroenterology. May-Jun. 2002;49(45):709-14. Database BIOSIS Abstract. Accession No. PREV200200382020 and full text. Abstract and full text.

Skurkovich et al., Treatment of corneal transplant rejection in humans with anti-interferon-gamma antibodies. Am J Ophthalmol. Jun. 2002;133(6):829-30.

Smith et al., Prolonged in vivo residence times of antibody fragments associated with albumin. Bioconjug Chem. Sep.-Oct. 2001;12(5):750-6.

Smith-Gill et al., Contributions of immunoglobulin heavy and light chains to antibody specificity for lysozyme and two haptens. J Immunol. Dec. 15, 1987;139(12):4135-44.

Sollinger et al., Basiliximab versus antithymocyte globulin for prevention of acute renal allograft rejection. Transplantation. Dec. 27, 2001;72(12):1915-9.

Song et al., Light chain of natural antibody plays a dominant role in protein antigen binding. Biochem Biophys Res Commun. Feb. 16, 2000;268(2):390-4.

Spinelli et al., The crystal structure of a llama heavy chain variable domain. Nat Struct Biol. Sep. 1996;3(9):752-7.

Tang et al., Stabilization of leucine zipper coiled coils by introduction of trifluoroleucine. Abst Pap Am Chem. 1999;S218:U138-U138. Abstract 416.

Tanha et al., Selection by phage display of llama conventional V(H) fragments with heavy chain antibody V(H)H properties. J Immunol Methods. May 1, 2002;263(1-2):97-109.

Teitelbaum et al., A mAb recognizing a surface antigen of Mycobacterium tuberculosis enhances host survival. Proc Natl Acad Sci U S A. Dec. 22, 1998;95(26):15688-93.

Vajdos et al., Comprehensive functional maps of the antigen-binding site of an anti-ErbB2 antibody obtained with shotgun scanning mutagenesis. J Mol Biol. Jul. 5, 2002;320(2):415-28.

Van Der Linden et al., Comparison of physical chemical properties of llama VHH antibody fragments and mouse monoclonal antibodies. Biochim Biophys Acta. Apr. 12, 1999;1431(1):37-46.

Van Hest et al., Efficient introduction of alkene functionality into proteins in vivo. FEBS Lett. May 22, 1998;428(1-2):68-70.

Vincke et al., General strategy to humanize a camelid single-domain antibody and identification of a universal humanized nanobody scaffold. J Biol Chem. Jan. 30, 2009;284(5):3273-84. Epub Nov. 14, 2008.

Vu et al., Comparison of llama VH sequences from conventional and heavy chain antibodies. Mol Immunol. Nov.-Dec. 1997;34(16-17):1121-31.

Ward et al., Binding activities of a repertoire of single immunoglobulin variable domains secreted from *Escherichia coli*. Nature. Oct. 12, 1989;341(6242):544-6.

Winkler et al., Changing the antigen binding specificity by single point mutations of an anti-p24 (HIV-1) antibody. J Immunol. Oct. 15, 2000;165(8):4505-14.

Worledge et al., Oral administration of avian tumor necrosis factor antibodies effectively treats experimental colitis in rats. Dig Dis Sci. Dec. 2000;45(12):2298-305.

Wu et al., Humanization of a murine monoclonal antibody by simultaneous optimization of framework and CDR residues. J Mol Biol. Nov. 19, 1999;294(1):151-62.

[No author listed] Anti human IgG ligand for depletion of human plasma. Biotechnol App Centre. Sep. 2003 Product sheet 101-0822-V1.0. www.bac.nl. 2 pages.

[No author listed] Anti human serum albumin ligand for depletion of human plasma. Biotechnol App Centre. Sep. 2003 Product sheet 102-0826-V1.0. www.bac.nl. 2 pages.

[No author listed] BAC invoice (redacted) for 102-0822-03 CaptureSelect anti-human IgG ligand. Invoice number: S05-0006. Invoice date: Mar. 24, 2005. 1 page.

Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

Hasemann et al., Mutational analysis of arsonate binding by a CRIA+ antibody. VH and VL junctional diversity are essential for binding activity. J Biol Chem. Apr. 25, 1991;266(12):7626-32.

Ibragimova et al., Stability of the beta-sheet of the WW domain: A molecular dynamics simulation study. Biophys J. Oct. 1999;77(4):2191-8.

Krauss et al., Impact of antibody framework residue VH-71 on the stability of a humanised anti-MUC1 scFv and derived immunoenzyme. Br J Cancer. May 4, 2004;90(9):1863-70.

Lazar et al., Transforming growth factor alpha: mutation of aspartic acid 47 and leucine 48 results in different biological activities. Mol Cell Biol. Mar. 1988;8(3):1247-52.

Lin et al., Structure-function relationships in glucagon: properties of highly purified Des-His1-, monoiodo-, and (Des-Asn28,Thr29)(homoserine lactone27)-glucagon. Biochemistry. Apr. 22, 1975;14(8):1559-63.

Pakula et al., Genetic analysis of protein stability and function. Annu Rev Genet. 1989;23:289-310. Summary only.

Roitt et al., Immunology. MIR. Moscow. 2000; p. 150. Russian with English Translation.

Schwartz et al., A superactive insulin: [B10-aspartic acid]insulin(human). Proc Natl Acad Sci U S A. Sep. 1987;84(18):6408-11.

* cited by examiner

SERUM ALBUMIN BINDING PROTEINS

RELATED APPLICATIONS

This application is a national stage filing under 35 U.S.C. §371 of international application PCT/EP2006/004679, filed May 17, 2006, and claims the benefit under 35 U.S.C. §119(e) of U.S. provisional application Ser. No. 60/682,332, filed May 18, 2005.

The present invention relates to amino acid sequences that are capable of binding to serum albumin; to proteins and polypeptides comprising or essentially consisting of such amino acid sequences; to nucleic acids that encode such amino acid sequences, proteins or polypeptides; to compositions, and in particular pharmaceutical compositions, that comprise such amino acid sequences, proteins and polypeptides; and to uses of such amino acid sequences, proteins and polypeptides.

Other aspects, embodiments, advantages and applications of the invention will become clear from the further description herein.

Amino acid sequences that are capable of binding to human serum albumin and uses thereof in polypeptide constructs in order to increase the half-life of therapeutically relevant proteins and polypeptides are known in the art.

For example, WO 91/01743, WO 01/45746 and WO 02/076489 describe peptide moieties binding to serum albumin that can be fused to therapeutic proteins and other therapeutic compounds and entities in order to increase the half-life thereof. However, these peptide moieties are of bacterial or synthetic origin, which is less preferred for use in therapeutics.

WO 04/041865 by applicant describes Nanobodies® directed against serum albumin (and in particular against human serum albumin) that can be linked to other proteins (such as one or more other Nanobodies® directed against a desired target) in order to increase the half-life of said protein.

The neonatal Fc receptor (FcRn), also termed "Brambell receptor", is involved in prolonging the life-span of albumin in circulation (see Chaudhury et al., The Journal of Experimental Medicine, vol. 3, no. 197, 315-322 (2003)). The FcRn receptor is an integral membrane glycoprotein consisting of a soluble light chain consisting of β2-microglobulin, noncovalently bound to a 43 kD α chain with three extracellular domains, a transmembrane region and a cytoplasmic tail of about 50 amino acids. The cytoplasmic tail contains a dinucleotide motif-based endocytosis signal implicated in the internalization of the receptor. The α chain is a member of the nonclassical MHC I family of proteins. The β2m association with the α chain is critical for correct folding of FcRn and exiting the endoplasmic reticulum for routing to endosomes and the cell surface.

The overall structure of FcRn is similar to that of class I molecules. The α-1 and α-2 regions resemble a platform composed of eight antiparallel β strands forming a single β-sheet topped by two antiparallel α-helices very closely resembling the peptide cleft in MHC I molecules. Owing to an overall repositioning of the α-1 helix and bending of the C-terminal portion of the α-2 helix due to a break in the helix introduced by the presence of Pro162, the FcRn helices are considerably closer together, occluding peptide binding. The side chain of Arg164 of FcRn also occludes the potential interaction of the peptide N-terminus with the MHC pocket. Further, salt bridge and hydrophobic interaction between the α-1 and α-2 helices may also contribute to the groove closure.

FcRn therefore, does not participate in antigen presentation, and the peptide cleft is empty.

FcRn binds and transports IgG across the placental syncytiotrophoblast from maternal circulation to fetal circulation and protects IgG from degradation in adults. In addition to homeostasis, FcRn controls transcytosis of IgG in tissues. FcRn is localized in epithelial cells, endothelial cells and hepatocytes.

According to Chaudhury et al. (supra), albumin binds FcRn to form a tri-molecular complex with IgG. Both albumin and IgG bind noncooperatively to distinct sites on FcRn. Binding of human FcRn to Sepharose-HSA and Sepharose-hIgG was pH dependent, being maximal at pH 5.0 and nil at pH 7.0 through pH 8. The observation that FcRn binds albumin in the same pH dependent fashion as it binds IgG suggests that the mechanism by which albumin interacts with FcRn and thus is protected from degradation is identical to that of IgG, and mediated via a similarly pH-sensitive interaction with FcRn. Using SPR to measure the capacity of individual HSA domains to bind immobilized soluble hFcRn, Chaudhury showed that FcRn and albumin interact via the D-III domain of albumin in a pH-dependent manner, on a site distinct from the IgG binding site (Chaudhury, PhD dissertation, see www.andersonlab.com/biosketchCC.htm; Chaudhury et al. Biochemistry, ASAP Article 10.1021/bi052628y S0006-2960(05)02628-0 (Web release date: Mar. 22, 2006)).

It is an object of the present invention to provide amino acid sequences that are an alternative, and in particular an improved alternative, to the albumin-binding amino acid sequences described in the prior art cited above.

In one aspect, the invention achieves this objective by providing amino acid sequences, and in particular immunoglobulin sequences, and more in particular immunoglobulin variable domain sequences, that can bind to or otherwise associate with serum albumin in such a way that, when the amino acid sequence or polypeptide construct is bound to or otherwise associated with a serum albumin molecule, the binding of said serum albumin molecule to FcRn is not (significantly) reduced or inhibited (i.e. compared to the binding of said serum albumin molecule to FcRn when the amino acid sequence or polypeptide construct is not bound thereto). In this aspect of the invention, by "not significantly reduced or inhibited" is meant that the binding affinity for serum albumin to FcRn (as measured using a suitable assay, such as SPR) is not reduced by more than 50%, preferably not reduced by more than 30%, even more preferably not reduced by more than 10%, such as not reduced by more than 5%, or essentially not reduced at all. In this aspect of the invention, "not significantly reduced or inhibited" may also mean (or additionally mean) that the half-life of the serum albumin molecule is not significantly reduced (as defined below).

When in this description, reference is made to binding, such binding is preferably specific binding, as normally understood by the skilled person.

When an amino acid sequence as described herein is a monovalent immunoglobulin sequence (for example, a monovalent Nanobody), said monovalent immunoglobulin sequence preferably binds to human serum albumin with a dissociation constant (KD) of $10^{-5}$ to $10^{-12}$ moles/liter or less, and preferably $10^{-7}$ to $10^{-12}$ moles/liter or less and more preferably $10^{-8}$ to $10^{-12}$ moles/liter, and/or with a binding affinity of at least $10^7$ M−1, preferably at least $10^8$ M−1, more preferably at least $10^9$ M−1, such as at least $10^{12}$ M−1. Any KD value greater than $10^{-4}$ liters/mol is generally considered to indicate non-specific binding. Preferably, a monovalent immunoglobulin sequence of the invention will bind to the desired antigen with an affinity less than 500 mM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art.

In another aspect, the invention provides amino acid sequences, and in particular immunoglobulin sequences, and more in particular immunoglobulin variable domain sequences, that can bind to or otherwise associate with serum albumin in such a way that, when the amino acid sequence or polypeptide construct is bound to or otherwise associated with a serum albumin molecule, the half-life of the serum albumin molecule is not (significantly) reduced (i.e. compared to the half-life of the serum albumin molecule when the amino acid sequence or polypeptide construct is not bound thereto). In this aspect of the invention, by "not significantly reduced" is meant that the half-life of the serum albumin molecule (as measured using a suitable technique known per se) is not reduced by more than 50%, preferably not reduced by more than 30%, even more preferably not reduced by more than 10%, such as not reduced by more than 5%, or essentially not reduced at all.

In another aspect, the invention provides amino acid sequences, and in particular immunoglobulin sequences, and more in particular immunoglobulin variable domain sequences, that are capable of binding to amino acid residues on serum albumin that are not involved in binding of serum albumin to FcRn. More in particular, this aspect of the invention provides amino acid sequences that are capable of binding to amino acid sequences of serum albumin that do not form part of domain III of serum albumin. For example, but without being limited thereto, this aspect of the invention provides amino acid sequences that are capable of binding to amino acid sequences of serum albumin that form part of domain I and/or domain II.

The amino acid sequences of the invention are preferably (single) domain antibodies or suitable for use as (single) domain antibodies, and as such may be heavy chain variable domain sequence (VH sequence) or a light chain variable domain sequence (VL sequence), and preferably are VH sequences. The amino acid sequences may for example be so-called "dAb's".

However, according to a particularly preferred embodiment, the amino acid sequences of the present invention are Nanobodies. For a further description and definition of Nanobodies, as well as of some of the further terms used in the present description, reference is made to the copending patent applications by applicant (such as the copending International application by applicant entitled "Improved Nanobodies™ against Tumor Necrosis Factor-alpha", which has the same priority and the same international filing date as the present application); as well as the further prior art cited therein.

As such, they may be Nanobodies belonging to the "KERE"-class, to the "GLEW"-class or to the "103-P,R,S"-class (again as defined in the copending patent applications by applicant).

Preferably, the amino acid sequences of the present invention are humanized Nanobodies (again as defined in the copending patent applications by applicant).

The amino acid sequences disclosed herein can be used with advantage as a fusion partner in order to increase the half-life of therapeutic moieties such as proteins, compounds (including, without limitation, small molecules) or other therapeutic entities.

Thus, in another aspect, the invention provides proteins or polypeptides that comprise or essentially consist of an amino acid sequence as disclosed herein. In particular, the invention provides protein or polypeptide constructs that comprise or essentially consist of at least one amino acid sequence of the invention that is linked to at least one therapeutic moiety, optionally via one or more suitable linkers or spacers. Such protein or polypeptide constructs may for example (without limitation) be a fusion protein, as further described herein.

The invention further relates to therapeutic uses of protein or polypeptide constructs or fusion proteins and constructs and to pharmaceutical compositions comprising such protein or polypeptide constructs or fusion proteins.

In some embodiments the at least one therapeutic moiety comprises or essentially consists of a therapeutic protein, polypeptide, compound, factor or other entity. In a preferred embodiment the therapeutic moiety is directed against a desired antigen or target, is capable of binding to a desired antigen (and in particular capable of specifically binding to a desired antigen), and/or is capable of interacting with a desired target. In another embodiment, the at least one therapeutic moiety comprises or essentially consists of a therapeutic protein or polypeptide. In a further embodiment, the at least one therapeutic moiety comprises or essentially consists of an immunoglobulin or immunoglobulin sequence (including but not limited to a fragment of an immunoglobulin), such as an antibody or an antibody fragment (including but not limited to an ScFv fragment). In yet another embodiment, the at least one therapeutic moiety comprises or essentially consists of an antibody variable domain, such as a heavy chain variable domain or a light chain variable domain.

In a preferred embodiment, the at least one therapeutic moiety comprises or essentially consists of at least one domain antibody or single domain antibody, "dAb" or Nanobody®. According to this embodiment, the amino acid sequence of the invention is preferably also a domain antibody or single domain antibody, "dAb" or Nanobody, so that the resulting construct or fusion protein is a multivalent construct (as described herein) and preferably a multispecific construct (also as defined herein) comprising at least two domain antibodies, single domain antibodies, "dAbs" or Nanobodies® (or a combination thereof), at least one of which is directed against (as defined herein) serum albumin.

In a specific embodiment, the at least one therapeutic moiety comprises or essentially consists of at least one monovalent Nanobody® or a bivalent, multivalent, bispecific or multispecific Nanobody® construct. According to this embodiment, the amino acid sequence of the invention is preferably also a Nanobody, so that the resulting construct or fusion protein is a multivalent Nanobody construct (as described herein) and preferably a multispecific Nanobody construct (also as defined herein) comprising at least two Nanobodies, at least one of which is directed against (as defined herein) serum albumin.

According to one embodiment of the invention, the Nanobody against human serum albumin is a humanized Nanobody.

Also, when the amino acid sequences, proteins, polypeptides or constructs of the invention are intended for pharmaceutical or diagnostic use, the aforementioned are preferably directed against human serum albumin. According to one preferred, but non-limiting embodiment, the amino acid sequences, proteins, polypeptides or constructs show an affinity for human serum albumin that is higher than the affinity for mouse serum albumin (determined as described in the Experimental Part).

According to one preferred, but non-limiting embodiment, the amino acid sequence of the invention is directed to the same epitope on human serum albumin as clone PMP6A6 (ALB-1).

According to a specific, but non-limiting embodiment, the amino acid sequence of the invention is an immunoglobulin sequence (and preferably a Nanobody) that is capable of binding to human serum albumin that consists of 4 framework regions (FR1 to FR4 respectively) and 3 complementarity determining regions (CDR1 to CDR3 respectively), in which:
a) CDR1 is an amino acid sequence chosen from the group consisting of the CDR1 sequences of SEQ ID NOS: 8 to 14 and/or from the group consisting of amino acid sequences that have 2 or only 1 "amino acid difference(s)" (as defined herein) with one of the CDR1 sequences of SEQ ID NOS 8 to 14;

and in which the framework sequences may be any suitable framework sequences, such as the framework sequences of a (single) domain antibody and in particular of a Nanobody.

In the above amino acid sequences:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequences.

Some preferred combinations of CDR sequences in the Nanobodies of the invention, and some preferred combinations of CDR and framework sequences in the Nanobodies of the invention, can be seen from Table I below.

Table II below lists some preferred Nanobodies of the invention. Table III below lists some preferred humanized Nanobodies of the invention.

TABLE I preferred combinations of CDR sequences, and preferred combination of CDR sequence and framework sequences.

| CLONE | | ID | FR1 | ID | CDR1 | ID | FR2 | ID | CDR2 |
|---|---|---|---|---|---|---|---|---|---|
| PMP6A8 | (ALB2) | 1 | AVQLVESGGGLVQGGGSLRLACAASERIFD | 8 | LNLMG | 15 | WYRQGPGNERELVA | 22 | TCITVGDSTNYADSVKG |
| PMP6B4 | | 2 | EVQLVESGGGLVQEGGSLRLACAASERIWD | 9 | INLLG | 16 | WYRQGPGNERELVA | 23 | TITVGDSTSYADSVKG |
| PMP6A6 | (ALB1) | 3 | AVQLVESGGGLVQPGNSLRLSCAASGFTFR | 10 | SFGMS | 17 | WVRQAPGKEPEWVS | 24 | SISGSGSDTLYADSVKG |
| PMP6C1 | | 4 | AVQLVDSGGGLVQPGGSLRLSCAASGFSFG | 11 | SFGMS | 18 | WVRQYPGKEPEWVS | 25 | SINGRGDDTRYADSVKG |
| PMP6G8 | | 5 | AVQLVESGGGLVQPGGSLRLTCTASGFTFR | 12 | SFGMS | 19 | WVRQAPGKDQEWVS | 26 | AISADSSTKNYADSVKG |
| PMP6A5 | | 6 | QVQLAESGGGLVQPGGSLRLTCTASGFTFG | 13 | SFGMS | 20 | WVRQAPGEGLEWVS | 27 | AISADSSDKRYADSVKG |
| PMP6G7 | | 7 | QVQLVESGGGLVQPGGSLRLSCAASGFTFS | 14 | NYWMY | 21 | WVRVAPGKGLERIS | 28 | RDISTGGGYSYYADSVKG |

| CLONE | | ID | FR3 | ID | CDR3 | ID | FR4 |
|---|---|---|---|---|---|---|---|
| PMP6A8 | (ALB2) | 29 | RFTISMDYTKQTVYLHMNSLRPEDTGLYYCKI | 36 | RRTWHSEL | 43 | WGQGTQVTVSS |
| PMP6B4 | | 30 | RFTISRDYDKNTLYLQMNSLRPEDTGLYYCKI | 37 | RRTWHSEL | 44 | WGQGTQVTVSS |
| PMP6A6 | (ALB1) | 31 | RFTISRDNAKTTLYLQMNSLKPEDTAVYYCTI | 38 | GGSLSR | 45 | SSQGTQVTVSS |
| PMP6CI | | 32 | RFSISRDNAKNTLYLQMNSLKPEDTAEYYCTI | 39 | GRSVSRS | 46 | RTQGTQVTVSS |
| PMP6G8 | | 33 | RFTISRDNAKKMLYLEMNSLKPEDTAVYYCVI | 40 | GRGSP | 47 | SSPGTQVTVSS |
| PMP6A5 | | 34 | RFTISRDNAKKMLYLEMNSLKSEDTAVYYCVI | 41 | GRGSP | 48 | ASQGTQVTVSS |
| PMP6G7 | | 35 | RFTISRDNAKNTLYLQMNSLKPEDTALYYCAK | 42 | DREAQVDTLDFDY | 49 | RGQGTQVTVSS | and in which:
b) CDR2 is an amino acid sequence chosen from the group consisting of the CDR2 sequences of SEQ ID NOS: 22 to 29; or from the group consisting of amino acid sequences that have at least 80%, preferably at least 90%, more preferably at least 95%, even more preferably at least 99% sequence identity (as defined herein) with one of the CDR2 sequences of SEQ ID NOS: 22 to 29; and/or from the group consisting of amino acid sequences that have 2 or only 1 "amino acid difference(s)" (as defined herein) with one of the CDR2 sequences of SEQ ID NOS 22 to 29;
and in which:
c1) CDR3 is an amino acid sequence chosen from the group consisting of the CDR3 sequence of SEQ ID NO: 42; the amino acid sequences that have at least 80%, preferably at least 90%, more preferably at least 95%, even more preferably at least 99% sequence identity (as defined herein) with the CDR3 sequence of SEQ ID NO: 42; and the amino acid sequences that have 3, 2 or only 1 "amino acid difference(s)" with the CDR3 sequence of SEQ ID NO:42;
or alternatively in which:
c2) CDR3 is an amino acid sequence chosen from the group consisting of the CDR3 sequences of SEQ ID NOS: 36 to 41 and/or from the group consisting of amino acid sequences that have 2 or only 1 "amino acid difference(s)" (as defined herein) with one of the CDR1 sequences of SEQ ID NOS: 36 to 41;

TABLE II preferred, but non-limiting Nanobodies of the invention.

| | | |
|---|---|---|
| PMP6A8 (ALB2) | 50 | AVQLVESGGGLVQGGGSLRLACAASERIFDLNLMGWYRQGP GNERELVATCITVG.DSTNYADSVKGRFTISMDYTKQTVYL HMNSLRPEDTGLYYCKIRRTWHSELWGQGTQVTVSS |
| PMP6B4 | 51 | EVQLVESGGGLVQEGGSLRLACAASERIWDINLLGWYRQGP GNERELVATITVG.DSTSYADSVKGRFTISRDYDKNTLYLQ MNSLRPEDTGLYYCKIRRTWHSELWGQGTQVTVSS |
| PMP6A6 (ALB1) | 52 | AVQLVESGGGLVQPGNSLRLSCAASGFTFRSFGMSWVRQAP GKEPEWVSSISGSGSDTLYADSVKGRFTISRDNAKTTLYLQ MNSLKPEDTAVYYCTIGGSLSRSSQGTQVTVSS |
| PMP6C1 | 53 | AVQLVDSGGGLVQPGGSLRLSCAASGFSFGSFGMSWVRQYP GKEPEWVSSINGRGDDTRYADSVKGRFSISRDNAKNTLYLQ MNSLKPEDTAEYYCTIGRSVSRSRTQGTQVTVSS |
| PMP6G8 | 54 | AVQLVESGGGLVQPGGSLRLTCTASGFTFRSFGMSWVRQAP GKDQEWVSAISADSSTKNYADSVKGRFTISRDNAKKMLYLE MNSLKPEDTAVYYCVIGRGSPSSPGTQVTVSS |
| PMP6A5 | 55 | QVQLAESGGGLVQPGGSLRLTCTASGFTFGSFGMSWVRQAP GEGLEWVSAISADSSDKRYADSVKGRFTISRDNAKKMLYLE MNSLKSEDTAVYYCVIGRGSPASQGTQVTVSS |
| PMP6G7 | 56 | QVQLVESGGGLVQPGGSLRLSCAASGFTFSNYWMYWVRVAP GKGLERISRDISTGGGYSYYADSVKGRFTISRDNAKNTLYL QMNSLKPEDTALYYCAKDREAQVDTLDFDYRGQGTQVTVSS |

TABLE III preferred, but non-limiting humanized Nanobodies of the invention.

| | | |
|---|---|---|
| ALB3 (ALB1 HUM1) | 57 | EVQLVESGGGLVQPGGSLRLSCAASGFTFRSFGMSWVRQAP GKEPEWVSSISGSGSDTLYADSVKGRFTISRDNAKTTLYLQ MNSLKPEDTAVYYCTIGGSLSRSSQGTQVTVSS |
| ALB4 (ALB1 HUM2) | 58 | EVQLVESGGGLVQPGGSLRLSCAASGFTFSSFGMSWVRQAP GKEPEWVSSISGSGSDTLYADSVKGRFTISRDNAKTTLYLQ MNSLKPEDTAVYYCTIGGSLSRSSQGTQVTVSS |
| ALB5 (ALB1 HUM3) | 59 | EVQLVESGGGLVQPGGSLRLSCAASGFTFRSFGMSWVRQAP GKGLEWVSSISGSGSDTLYADSVKGRFTISRDNAKTTLYLQ MNSLKPEDTAVYYCTIGGSLSRSSQGTQVTVSS |
| ALB6 (ALB1 HUM1) | 60 | EVQLVESGGGLVQPGNSLRLSCAASGFTFRSFGMSWVRQAP GKGLEVVSSISGSGSDTLYADSVKGRFTISRDNAKTTLYLQ MNSLKPEDTAVYYCTIGGSLSRSSQGTLVTVSS |
| ALB7 (ALB1 HUM2) | 61 | EVQLVESGGGLVQPGNSLRLSCAASGFTFRSFGMSWVRQAP GKGLEWVSSISGSGSDTLYADSVKGRFTISRDNAKTTLYLQ MNSLRPEDTAVYYCTIGGSLSRSSQGTLVTVSS |
| ALB8 (ALB1 HUM3) | 62 | EVQLVESGGGLVQPGNSLRLSCAASGFTFSSFGMSWVRQAP GKGLEWVSSISGSGSDTLYADSVKGRFTISRDNAKTTLYLQ MNSLRPEDTAVYYCTIGGSLSRSSQGTLVTVSS |
| ALB9 (ALB1 HUM4) | 63 | EVQLVESGGGLVQPGNSLRLSCAASGFTFSSFGMSWVRQAP GKGLEWVSSISGSGSDTLYADSVKGRFTISRDNAKNTLYLQ MNSLRPEDTAVYYCTIGGSLSRSSQGTLVTVSS |
| ALB10 (ALB1 HUM5) | 64 | EVQLVESGGGLVQPGNSLRLSCAASGFTFSSFGMSWVRQAP GKGLEWVSSISGSGSDTLYADSVKGRFTISRDNAKNTLYLQ MNSLRPEDTAVYYCTIGGSLSRSGQGTLVTVSS |

Thus, in another aspect, an amino acid sequence of the invention is a Nanobody, which has at least 80%, preferably at least 90%, more preferably at least 95%, even more preferably at least 99% sequence identity (as defined herein) with at least one of the amino acid sequences of SEQ ID NO's 50 to 64.

Thus, in another aspect, an amino acid sequence of the invention is a Nanobody, which has at least 80%, preferably at least 90%, more preferably at least 95%, even more preferably at least 99% sequence identity (as defined herein) with at least one of the amino acid sequences of SEQ ID NO's 50 to 64, in which:
  the CDR1 sequences present in such Nanobodies are chosen from the CDR1 sequences of SEQ ID NOS: 8 to 14 or from amino acid sequences with only 1 amino acid difference with such a CDR1 sequence;
  the CDR2 sequences present in such Nanobodies are chosen from the CDR1 sequences of SEQ ID NOS: 22 to 28 or from amino acid sequences with only 1 amino acid difference with such a CDR2 sequence;
  and the CDR1 sequences present in such Nanobodies are chosen from the CDR1 sequences of SEQ ID NOS: 23 to 42 or from amino acid sequences with only 1 amino acid difference with such a CDR3 sequence.

In another aspect, an amino acid sequence of the invention is a Nanobody, which has at least 80%, preferably at least 90%, more preferably at least 95%, even more preferably at least 99% sequence identity (as defined herein) with at least one of the amino acid sequences of SEQ ID NO's 50 to 64, in which:
  the CDR1 sequences present in such Nanobodies are chosen from the CDR1 sequences of SEQ ID NOS: 8 to 14;
  the CDR2 sequences present in such Nanobodies are chosen from the CDR1 sequences of SEQ ID NOS: 22 to 28;
  and the CDR1 sequences present in such Nanobodies are chosen from the CDR1 sequences of SEQ ID NOS: 23 to 42.

One particularly preferred group of Nanobodies for use in the present invention comprises clone PMP6A6 (ALB1; SEQ ID NO: 52) and humanized variants thereof, including but not limited to the clones ALB 3 (SEQ ID NO: 57); ALB 4 (SEQ ID NO: 58); ALB 5 (SEQ ID NO: 59); ALB 6 (SEQ ID NO: 60); ALB 7 (SEQ ID NO: 61); ALB 8 (SEQ ID NO: 62); ALB 9 (SEQ ID NO: 63); and ALB 10 (SEQ ID NO: 64), of which ALB 8 (SEQ ID NO: 62) is particularly preferred.

Thus, in one preferred aspect, the invention relates to an amino acid sequence, which has at least 80%, preferably at least 90%, more preferably at least 95%, even more preferably at least 99% sequence identity (as defined herein) with at least one of the amino acid sequences of SEQ ID NO's 52 and 57 to 64.

In another preferred aspect, the amino acid sequence of the invention is an immunoglobulin sequence (and preferably a Nanobody) that is capable of binding to human serum albumin that consists of 4 framework regions (FR1 to FR4 respectively) and 3 complementarity determining regions (CDR1 to CDR3 respectively), in which:
a) CDR1 comprises, is or essentially consists of:
  the amino acid sequence SFGMS (SEQ ID NO:10); or
  an amino acid sequence that has at least 80%, preferably at least 90%, more preferably at least 95%, even more preferably at least 99% sequence identity with the amino acid sequence SFGMS (SEQ ID NO:10); or
  an amino acid sequences that has 2 or only 1 amino acid difference(s) with the amino acid sequence SFGMS (SEQ ID NO:10);
and in which:
a) CDR2 comprises, is or essentially consists of:
  the amino acid sequence SISGSGSDTLYADSVKG (SEQ ID NO:24); or
  an amino acid sequence that has at least 80%, preferably at least 90%, more preferably at least 95%, even more preferably at least 99% sequence identity with the amino acid sequence SISGSGSDTLYADSVKG (SEQ ID NO:24); or
  an amino acid sequences that has 2 or only 1 amino acid difference(s) with the amino acid sequence SISGSGSDTLYADSVKG (SEQ ID NO:24);
and in which:
b) CDR3 comprises, is or essentially consists of:
  the amino acid sequence GGSLSR (SEQ ID NO:38); or
  an amino acid sequence that has at least 80%, preferably at least 90%, more preferably at least 95%, even more preferably at least 99% sequence identity with the amino acid sequence GGSLSR (SEQ ID NO:38); or
  an amino acid sequences that has 2 or only 1 amino acid difference(s) with the amino acid sequence GGSLSR (SEQ ID NO:38).

In particular, the invention relates to such a Nanobody, in which:
  CDR1 comprises or is the amino acid sequence SFGMS (SEQ ID NO:10);
  or in which
  CDR2 comprises or is the amino acid sequence SISGSGSDTLYADSVKG (SEQ ID NO:24);
  or in which:
  CDR3 comprises or is the amino acid sequence SPSGFN (SEQ ID NO:65).

More in particular, the invention relates to such a Nanobody, in which
  CDR1 comprises or is the amino acid sequence SFGMS (SEQ ID NO:10); and
  CDR3 comprises or is comprises the amino acid sequence GGSLSR (SEQ ID NO:38);

or in which:
CDR1 comprises or is the amino acid sequence SFGMS (SEQ ID NO:10); and
CDR2 comprises or is the amino acid sequence SISGSGS-DTLYADSVKG (SEQ ID NO:24);
or in which:
CDR2 comprises or is the amino acid sequence SISGSGS-DTLYADSVKG (SEQ ID NO:24); and CDR3 comprises or is the amino acid sequence GGSLSR (SEQ ID NO:38).

Even more in particular, the invention relates to such a Nanobody, in which CDR1 comprises or is the amino acid sequence SFGMS (SEQ ID NO:10); CDR2 comprises or is the amino acid sequence SISGSGSDTLYADSVKG (SEQ ID NO:24) and CDR3 comprises or is the amino acid sequence GGSLSR (SEQ ID NO:38).

These amino acid sequences again preferably have at least 80%, preferably at least 90%, more preferably at least 95%, even more preferably at least 99% sequence identity (as defined herein) with at least one of the amino acid sequences of SEQ ID NO's 52 and 57 to 64.

Also, again, these amino acid sequences are preferably humanized, as described in the co-pending applications by applicant. Some preferred humanizing substitutions will be clear from the skilled person, for example from comparing the non-humanized sequence of SEQ ID NO: 52 with the corresponding humanized sequences of SEQ ID NOS: 57-64.

When the amino acid sequence is an immunoglobulin sequence such as a immunoglobulin variable domain sequence, a suitable (i.e. suitable for the purposes mentioned herein) fragment of such a sequence may also be used. For example, when the amino acid sequence is a Nanobody, such a fragment may essentially be as described in WO 04/041865.

The invention also relates to a protein or polypeptide that comprises or essentially consists of an amino acid sequence as described herein, or a suitable fragment thereof.

As mentioned herein, the amino acid sequences described herein can be used with advantage as a fusion partner in order to increase the half-life of therapeutic moieties such as proteins, compounds (including, without limitation, small molecules) or other therapeutic entities. Thus, one embodiment of the invention relates to a construct or fusion protein that comprises at least one amino acid sequence of the invention and at least one therapeutic moieties. Such a construct or fusion protein preferably has increased half-life, compared to the therapeutic moiety per se. Generally, such fusion proteins and constructs can be (prepared and used) as described in the prior art cited above, but with an amino acid sequence of the invention instead of the half-life increasing moieties described in the prior art.

Generally, the constructs or fusion proteins described herein preferably have a half-life that is at least 1.5 times, preferably at least 2 times, such as at least 5 times, for example at least 10 times or more than 20 times, greater than the half-life of the corresponding therapeutic moiety per se.

Also, preferably, any such fusion protein or construct has a half-life that is increased with more than 1 hour, preferably more than 2 hours, more preferably of more than 6 hours, such as of more than 12 hours, compared to the half-life of the corresponding therapeutic moiety per se.

Also, preferably, any fusion protein or construct has a half-life that is more than 1 hour, preferably more than 2 hours, more preferably of more than 6 hours, such as of more than 12 hours, and for example of about one day, two days, one week, two weeks or three weeks, and preferably no more than 2 months, although the latter may be less critical.

Half-life can generally be defined as the time taken for the serum concentration of the polypeptide to be reduce by 50%, in vivo, for example due to degradation of the ligand and/or clearance or sequestration of the ligand by natural mechanisms. Methods for pharmacokinetic analysis and determination of half-life are familiar to those skilled in the art. Details may be found in Kenneth, A et al: Chemical Stability of Pharmaceuticals: A Handbook for Pharmacists and in Peters et al, Pharmacokinete analysis: A Practical Approach (1996). Reference is also made to "Pharmacokinetics", M Gibaldi & D Perron, published by Marcel Dekker, 2nd revised edition (1982).

Also, as mentioned above, when the amino acid sequence of the invention is a Nanobody, it can be used to increase the half-life of other immunoglobulin sequences, such as domain antibodies, single domain antibodies, "dAb's" or Nanobodies.

Thus, one embodiment of the invention relates to a construct or fusion protein that comprises at least one amino acid sequence of the invention and at least one immunoglobulin sequence, such as a domain antibodies, single domain antibodies, "dAb's" or Nanobodies. The immunoglobulin sequence is preferably directed against a desired target (which is preferably a therapeutic target), and/or another immunoglobulin sequence that useful or suitable for therapeutic, prophylactic and/or diagnostic purposes.

Thus, in another aspect, the invention relates to a multispecific (and in particular bispecific) Nanobody constructs that comprises at least one Nanobody as described herein, and at least one other Nanobody, in which said at least one other Nanobody is preferably directed against a desired target (which is preferably a therapeutic target), and/or another Nanobody that useful or suitable for therapeutic, prophylactic and/or diagnostic purposes.

For a general description of multivalent and multispecific polypeptides containing one or more Nanobodies and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 96/34103 and WO 99/23221. Some other examples of some specific multispecific and/or multivalent polypeptide of the invention can be found in the co-pending applications by applicant. In particular, for a general description of multivalent and multispecific constructs comprising at least one Nanobody against a serum protein for increasing the half-life, of nucleic acids encoding the same, of compositions comprising the same, of the preparation of the aforementioned, and of uses of the aforementioned, reference is made to the International application WO 04/041865 by applicant mentioned above. The amino acid sequences described herein can generally be used analogously to the half-life increasing Nanobodies described therein.

In one non-limiting embodiment, said other Nanobody is directed against tumor necrosis factor alpha (TNF-alpha), in monomeric and/or multimeric (i.e. trimeric) form. Some examples of such Nanobody constructs can be found in the copending International application by applicant entitled "Improved Nanobodies™ against Tumor Necrosis Factor-alpha", which has the same priority and the same international filing date as the present application.

The invention also relates to nucleotide sequences or nucleic acids that encode amino acid sequences, fusion proteins and constructs described herein. The invention further includes genetic constructs that include the foregoing nucleotide sequences or nucleic acids and one or more elements for genetic constructs known per se. The genetic construct may be in the form of a plasmid or vector. Again, such constructs can be generally as described in the co-pending patent applications by applicant described herein, such as WO 04/041862 or the copending International application by applicant entitled "Improved Nanobodies™ against Tumor Necrosis Factor-alpha".

The invention also relates to hosts or host cells that contain such nucleotide sequences or nucleic acids, and/or that express (or are capable of expressing), the amino acid sequences, fusion proteins and constructs described herein. Again, such host cells can be generally as described in the co-pending patent applications by applicant described herein, such as WO 04/041862 or the copending International application by applicant entitled "Improved Nanobodies™ against Tumor Necrosis Factor-alpha".

The invention also relates to a method for preparing an amino acid sequence, fusion protein or construct as described herein, which method comprises cultivating or maintaining a host cell as described herein under conditions such that said host cell produces or expresses an amino acid sequence, fusion protein or construct as described herein, and optionally further comprises isolating the amino acid sequence, fusion protein or construct so produced. Again, such methods can be performed as generally described in the co-pending patent applications by applicant described herein, such as WO 04/041862 or the copending International application by applicant entitled "Improved Nanobodies™ against Tumor Necrosis Factor-alpha".

The invention also relates to a pharmaceutical composition that comprises at least one amino acid sequence, fusion protein or construct as described herein, and optionally at least one pharmaceutically acceptable carrier, diluent or excipient. Such preparations, carriers, excipients and diluents may generally be as described in the co-pending patent applications by applicant described herein, such as WO 04/041862 or the copending International application by applicant entitled "Improved Nanobodies™ against Tumor Necrosis Factor-alpha".

However, since the amino acid sequences, fusion proteins or constructs described herein have an increased half-life, they are preferably administered to the circulation. As such, they can be administered in any suitable manner that allows the amino acid sequences, fusion proteins or constructs to enter the circulation, such as intravenously, via injection or infusion, or in any other suitable manner (including oral administration, administration through the skin, intranasal administration, administration via the lungs, etc) that allows the amino acid sequences, fusion proteins or constructs to enter the circulation. Suitable methods and routes of administration will be clear to the skilled person, again for example also from the teaching of WO 04/041862 or the copending International application by applicant entitled "Improved Nanobodies™ against Tumor Necrosis Factor-*alpha*"

Thus, in another aspect, the invention relates to a method for the prevention and/or treatment of at least one disease or disorder that can be prevented or treated by the use of a fusion protein or construct as described herein, which method comprises administering, to a subject in need thereof, a pharmaceutically active amount of a fusion protein or construct of the invention, and/or of a pharmaceutical composition comprising the same. The diseases and disorders that can be prevented or treated by the use of a fusion protein or construct as described herein will generally be the same as the diseases and disorders that can be prevented or treated by the use of the therapeutic moiety that is present in the fusion protein or construct of the invention.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

In another embodiment, the invention relates to a method for immunotherapy, and in particular for passive immunotherapy, which method comprises administering, to a subject suffering from or at risk of the diseases and disorders mentioned herein, a pharmaceutically active amount of a fusion protein or construct of the invention, and/or of a pharmaceutical composition comprising the same.

The fusion protein or construct and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific Nanobody or polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more fusion proteins or constructs of the invention, or of one or more compositions comprising the same, in one or more pharmaceutically effective amounts or doses. The specific amount(s) or doses to administered can be determined by the clinician, again based on the factors cited above.

Generally, for the prevention and/or treatment of the diseases and disorders mentioned herein and depending on the specific disease or disorder to be treated, the potency and/or the half-life of the specific fusion proteins or constructs to be used, the specific route of administration and the specific pharmaceutical formulation or composition used, the Nanobodies and polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single Nanobody or polypeptide of the invention will be used. It is however within the scope of the invention to use two or more Nanobodies and/or polypeptides of the invention in combination.

The Nanobodies and polypeptides of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the Nanobodies and polypeptides of the invention may be used in combination with other pharmaceutically active compounds or principles that are or can be used for the prevention and/or treatment of the diseases and disorders that can be prevented or treated with the fusion proteins or constructs of the invention, and as a result of which a synergistic effect may or may not be obtained.

The effectiveness of the treatment regimen used according to the invention may be determined and/or followed in any manner known per se for the disease or disorder involved, as will be clear to the clinician. The clinician will also be able, where appropriate and or a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

EXPERIMENTAL PART

Example 1

Identification of Serum Albumin Specific Nanobodies

The albumin specific nanobodies were identified from a llama immunized with human serum albumin. Screening of individual nanobodies was performed by ELISA using human, rhesus and mouse albumin, yielding a panel of nanobodies cross-reacting with the serum albumin of various species.

Example 2

Biacore Analysis

Binding of nanobodies to serum albumin was characterised by surface plasmon resonance in a Biacore 3000 instrument. Serum albumin from different species was covalently bound to CM5 sensor chips surface via amine coupling until an increase of 250 response units was reached. Remaining reactive groups were inactivated. Nanobody binding was assessed at one concentration (1 in 20 diluted). Each nanobody was injected for 4 minutes at a flow rate of 45 μl/min to allow for binding to chip-bound antigen. Binding buffer without nanobody was sent over the chip at the same flow rate to allow spontaneous dissociation of bound nanobody for 4 hours. $K_{off}$-values were calculated from the sensorgrams obtained for the different nanobodies. The nanobodies tested are ranked according to $k_{off}$-values, see Table IV below:

TABLE IV

| Class | Human | Rhesus | Mouse |
|---|---|---|---|
| C | PMP6A8 | PMP6A8 | PMP6B4 |
| C | PMP6B4 | PMP6B4 | PMP6A8 |
| B | PMP6A6 | PMP6A6 | PMP6A6 |
| B | PMP6C1 | PMP6C1 | PMP6C1 |
| A | PMP6G8 | PMP6G8 | PMP6G8 |
| A | PMP6A5 | PMP6A5 | PMP6A5 |
| D | PMP6G7 | PMP6G7 | PMP6G7 |

In a follow-up experiment, binding was assayed as described above except that series of different concentrations were used. Each concentration was injected for 4 minutes at a flow rate of 45 μl/min to allow for binding to chip-bound antigen. Binding buffer without analyte was sent over the chip at the same flow rate to allow for dissociation of bound nanobody. After 15 minutes, remaining bound analyte was removed by injection of the regeneration solution (25 mM NaOH).

From the sensorgrams obtained for the different concentrations of each analyte KD-values were calculated via steady state affinity when equilibrium was reached.

Results are summarized in Table V. Cross-reactivity is observed for both ALB1 and ALB2. The highest affinity is observed for ALB2 on human and rhesus albumin. However, the difference in affinity for human/rhesus versus mouse serum albumin is more pronounced for ALB2 (factor 400), while for ALB1 a difference of a factor 12 is observed.

TABLE V

|  |  | Human albumin | Rhesus albumin | Mouse albumin |
|---|---|---|---|---|
| ALB1 | KD (nM) | 0.57 | 0.52 | 6.5 |
|  | ka (1/Ms) | 1.11E+06 | 1.05E+06 | 1.11E+06 |
|  | kd (1/s) | 6.30E−04 | 5.46E−04 | 7.25E−03 |
| ALB2 | KD (nM) | 0.092 | 0.036 | 15.7 |
|  | ka (1/Ms) | 8.15E+05 | 1.94E+06 | 1.95E+05 |
|  | kd (1/s) | 7.52E−05 | 7.12E−05 | 3.07E−03 |

The invention claimed is:

1. An isolated amino acid sequence that is an immunoglobulin sequence and that can bind to serum albumin, in which:
   a) complementarity determining region 1 (CDR1) comprises or is SEQ ID NO:10; and in which:
   b) complementarity determining region 2 (CDR2) comprises or is SEQ ID NO:24; and in which:
   c) complementarity determining region 3 (CDR3) comprises or is SEQ ID NO:38.

2. The isolated amino acid sequence according to claim 1, which is a single domain antibody or an immunoglobulin variable domain sequence.

3. The isolated amino acid sequence according to claim 2, that is a $V_H$-, $V_L$- or $V_{HH}$-sequence.

4. The isolated amino acid sequence according to claim 2, which has at least 90% sequence identity with at least one of the amino acid sequences of SEQ ID NO's 50 to 64.

5. The isolated amino acid sequence according to claim 4, which is chosen from the group consisting of PMP6A6 (ALB1; SEQ ID NO: 52) and humanized variants thereof.

6. The isolated amino acid sequence according to claim 5, wherein the humanized variant of PMP6A6 (ALB1; SEQ ID NO: 52) is ALB 8 (SEQ ID NO: 62).

7. A fusion protein or construct, which comprises an amino acid sequence according to claim 1 and at least one therapeutic moiety.

8. The fusion protein or construct according to claim 7, in which the amino acid sequence is either directly linked to the at least one therapeutic moiety or is linked to the at least one therapeutic moiety via a linker or spacer.

9. The fusion protein or construct according to claim 7, in which the at least one therapeutic moiety comprises an immunoglobulin sequence or a fragment thereof.

10. The fusion protein or construct according to claim 9, in which the at least one therapeutic moiety comprises a single domain antibody or an immunoglobulin variable domain sequence.

11. A multivalent and multispecific polypeptide construct, comprising at least one amino acid sequence according to claim 1 which is an immunoglobulin variable domain sequence and at least one further immunoglobulin variable domain sequence.

12. The multivalent and multispecific polypeptide construct according to claim 11, in which the at least one amino acid sequence that is an immunoglobulin variable domain sequence is either directly linked to the at least one further immunoglobulin variable domain sequence or is linked to the at least one further immunoglobulin variable domain sequence via a linker or spacer.

13. The multivalent and multispecific polypeptide construct according to claim 11, in which the at least one amino acid sequence that is an immunoglobulin variable domain sequence is linked to the at least one further immunoglobulin variable domain sequence via a linker or spacer, and in which the linker is an amino acid sequence.

14. A pharmaceutical composition that comprises at least one amino acid sequence of claim 1, or a fusion protein or construct comprising the amino acid sequence of claim 1, and optionally at least one pharmaceutically acceptable carrier, diluent or excipient.

15. The isolated amino acid sequence according to claim 1, wherein the amino acid sequence binds to the same epitope on human serum albumin as PMP6A6 (ALB1; SEQ ID NO: 52).

16. The isolated amino acid sequence according to claim 1, wherein the amino acid sequence competes for binding to human serum albumin with PMP6A6 (ALB 1; SEQ ID NO: 52).

17. The isolated amino acid sequence according to claim 1, which has at least 90% sequence identity with at least one of the amino acid sequences of SEQ ID NOs: 52 or 57 to 64.

18. The isolated amino acid sequence according to claim 5, which is chosen from the group consisting of ALB 3 (SEQ ID NO: 57); ALB 4 (SEQ ID NO: 58); ALB 5 (SEQ ID NO: 59); ALB 6 (SEQ ID NO: 60); ALB 7 (SEQ ID NO: 61); ALB 8 (SEQ ID NO: 62); ALB 9 (SEQ ID NO: 63); and ALB 10 (SEQ ID NO: 64).

* * * * *

SEQUENCE LISTING

<160> NUMBER OF SEQ ID NOS: 65

<210> SEQ ID NO 1
<211> LENGTH: 30
<212> TYPE: PRT
<213> ORGANISM: Artificial

```
<220> FEATURE:
<223> OTHER INFORMATION: FRAMEWORK REGION 1; can be chemically
      synthesized

<400> SEQUENCE: 1

Ala Val Gln Leu Val Glu Ser Gly Gly Gly Leu Val Gln Gly Gly
1               5                   10                  15

Ser Leu Arg Leu Ala Cys Ala Ala Ser Glu Arg Ile Phe Asp
            20                  25                  30

<210> SEQ ID NO 2
<211> LENGTH: 30
<212> TYPE: PRT
<213> ORGANISM: Artificial
<220> FEATURE:
<223> OTHER INFORMATION: FRAMEWORK REGION 1; can be chemically
      synthesized

<400> SEQUENCE: 2

Glu Val Gln Leu Val Glu Ser Gly Gly Gly Leu Val Gln Glu Gly Gly
1               5                   10                  15

Ser Leu Arg Leu Ala Cys Ala Ala Ser Glu Arg Ile Trp Asp
            20                  25                  30

<210> SEQ ID NO 3
<211> LENGTH: 30
<212> TYPE: PRT
<213> ORGANISM: Artificial
<220> FEATURE:
<223> OTHER INFORMATION: FRAMEWORK REGION 1; can be chemically
      synthesized

<400> SEQUENCE: 3

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg
            20                  25                  30

<210> SEQ ID NO 4
<211> LENGTH: 30
<212> TYPE: PRT
<213> ORGANISM: Artificial
<220> FEATURE:
<223> OTHER INFORMATION: FRAMEWORK REGION 1; can be chemically
      synthesized

<400> SEQUENCE: 4

Ala Val Gln Leu Val Asp Ser Gly Gly Gly Leu Val Gln Pro Gly Gly
1               5                   10                  15

Ser Leu Arg Leu Ser Cys Ala Ala Ser Gly Phe Ser Phe Gly
            20                  25                  30

<210> SEQ ID NO 5
<211> LENGTH: 30
<212> TYPE: PRT
<213> ORGANISM: Artificial
<220> FEATURE:
<223> OTHER INFORMATION: FRAMEWORK REGION 1; can be chemically
      synthesized

<400> SEQUENCE: 5

Ala Val Gln Leu Val Glu Ser Gly Gly Gly Leu Val Gln Pro Gly Gly
1               5                   10                  15

Ser Leu Arg Leu Thr Cys Thr Ala Ser Gly Phe Thr Phe Arg
            20                  25                  30
```

```
<210> SEQ ID NO 6
<211> LENGTH: 30
<212> TYPE: PRT
<213> ORGANISM: Artificial
<220> FEATURE:
<223> OTHER INFORMATION: FRAMEWORK REGION 1; can be chemically
      synthesized

<400> SEQUENCE: 6

Gln Val Gln Leu Ala Glu Ser Gly Gly Gly Leu Val Gln Pro Gly Gly
1               5                   10                  15

Ser Leu Arg Leu Thr Cys Thr Ala Ser Gly Phe Thr Phe Gly
            20                  25                  30

<210> SEQ ID NO 7
<211> LENGTH: 30
<212> TYPE: PRT
<213> ORGANISM: Artificial
<220> FEATURE:
<223> OTHER INFORMATION: FRAMEWORK REGION 1; can be chemically
      synthesized

<400> SEQUENCE: 7

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 8
<211> LENGTH: 5
<212> TYPE: PRT
<213> ORGANISM: Artificial
<220> FEATURE:
<223> OTHER INFORMATION: COMPLEMENTARITY DETERMINING REGION 1; can be
      chemically synthesized

<400> SEQUENCE: 8

Leu Asn Leu Met Gly
1               5

<210> SEQ ID NO 9
<211> LENGTH: 5
<212> TYPE: PRT
<213> ORGANISM: Artificial
<220> FEATURE:
<223> OTHER INFORMATION: COMPLEMENTARITY DETERMINING REGION 1; can be
      chemically synthesized

<400> SEQUENCE: 9

Ile Asn Leu Leu Gly
1               5

<210> SEQ ID NO 10
<211> LENGTH: 5
<212> TYPE: PRT
<213> ORGANISM: Artificial
<220> FEATURE:
<223> OTHER INFORMATION: COMPLEMENTARITY DETERMINING REGION 1; can be
      chemically synthesized

<400> SEQUENCE: 10

Ser Phe Gly Met Ser
1               5

<210> SEQ ID NO 11
<211> LENGTH: 5
<212> TYPE: PRT
```

```
<213> ORGANISM: Artificial
<220> FEATURE:
<223> OTHER INFORMATION: COMPLEMENTARITY DETERMINING REGION 1; can be
      chemically synthesized

<400> SEQUENCE: 11

Ser Phe Gly Met Ser
1               5

<210> SEQ ID NO 12
<211> LENGTH: 5
<212> TYPE: PRT
<213> ORGANISM: Artificial
<220> FEATURE:
<223> OTHER INFORMATION: COMPLEMENTARITY DETERMINING REGION 1; can be
      chemically synthesized

<400> SEQUENCE: 12

Ser Phe Gly Met Ser
1               5

<210> SEQ ID NO 13
<211> LENGTH: 5
<212> TYPE: PRT
<213> ORGANISM: Artificial
<220> FEATURE:
<223> OTHER INFORMATION: COMPLEMENTARITY DETERMINING REGION 1; can be
      chemically synthesized

<400> SEQUENCE: 13

Ser Phe Gly Met Ser
1               5

<210> SEQ ID NO 14
<211> LENGTH: 5
<212> TYPE: PRT
<213> ORGANISM: Artificial
<220> FEATURE:
<223> OTHER INFORMATION: COMPLEMENTARITY DETERMINING REGION 1; can be
      chemically synthesized

<400> SEQUENCE: 14

Asn Tyr Trp Met Tyr
1               5

<210> SEQ ID NO 15
<211> LENGTH: 14
<212> TYPE: PRT
<213> ORGANISM: Artificial
<220> FEATURE:
<223> OTHER INFORMATION: FRAMEWORK REGION 2; can be chemically
      synthesized

<400> SEQUENCE: 15

Trp Tyr Arg Gln Gly Pro Gly Asn Glu Arg Glu Leu Val Ala
1               5                   10

<210> SEQ ID NO 16
<211> LENGTH: 14
<212> TYPE: PRT
<213> ORGANISM: Artificial
<220> FEATURE:
<223> OTHER INFORMATION: FRAMEWORK REGION 2; can be chemically
      synthesized

<400> SEQUENCE: 16

Trp Tyr Arg Gln Gly Pro Gly Asn Glu Arg Glu Leu Val Ala
1               5                   10
```

```
<210> SEQ ID NO 17
<211> LENGTH: 14
<212> TYPE: PRT
<213> ORGANISM: Artificial
<220> FEATURE:
<223> OTHER INFORMATION: FRAMEWORK REGION 2; can be chemically
      synthesized

<400> SEQUENCE: 17

Trp Val Arg Gln Ala Pro Gly Lys Glu Pro Glu Trp Val Ser
1               5                   10

<210> SEQ ID NO 18
<211> LENGTH: 14
<212> TYPE: PRT
<213> ORGANISM: Artificial
<220> FEATURE:
<223> OTHER INFORMATION: FRAMEWORK REGION 2; can be chemically
      synthesized

<400> SEQUENCE: 18

Trp Val Arg Gln Tyr Pro Gly Lys Glu Pro Glu Trp Val Ser
1               5                   10

<210> SEQ ID NO 19
<211> LENGTH: 14
<212> TYPE: PRT
<213> ORGANISM: Artificial
<220> FEATURE:
<223> OTHER INFORMATION: FRAMEWORK REGION 2; can be chemically
      synthesized

<400> SEQUENCE: 19

Trp Val Arg Gln Ala Pro Gly Lys Asp Gln Glu Trp Val Ser
1               5                   10

<210> SEQ ID NO 20
<211> LENGTH: 14
<212> TYPE: PRT
<213> ORGANISM: Artificial
<220> FEATURE:
<223> OTHER INFORMATION: FRAMEWORK REGION 2; can be chemically
      synthesized

<400> SEQUENCE: 20

Trp Val Arg Gln Ala Pro Gly Glu Gly Leu Glu Trp Val Ser
1               5                   10

<210> SEQ ID NO 21
<211> LENGTH: 14
<212> TYPE: PRT
<213> ORGANISM: Artificial
<220> FEATURE:
<223> OTHER INFORMATION: FRAMEWORK REGION 2; can be chemically
      synthesized

<400> SEQUENCE: 21

Trp Val Arg Val Ala Pro Gly Lys Gly Leu Glu Arg Ile Ser
1               5                   10

<210> SEQ ID NO 22
<211> LENGTH: 17
<212> TYPE: PRT
<213> ORGANISM: Artificial
<220> FEATURE:
<223> OTHER INFORMATION: COMPLEMENTARITY DETERMINING REGION 2; can be
      chemically synthesized

<400> SEQUENCE: 22
```

```
Thr Cys Ile Thr Val Gly Asp Ser Thr Asn Tyr Ala Asp Ser Val Lys
1               5                   10                  15

Gly

<210> SEQ ID NO 23
<211> LENGTH: 16
<212> TYPE: PRT
<213> ORGANISM: Artificial
<220> FEATURE:
<223> OTHER INFORMATION: COMPLEMENTARITY DETERMINING REGION 2; can be
      chemically synthesized

<400> SEQUENCE: 23

Thr Ile Thr Val Gly Asp Ser Thr Ser Tyr Ala Asp Ser Val Lys Gly
1               5                   10                  15

<210> SEQ ID NO 24
<211> LENGTH: 17
<212> TYPE: PRT
<213> ORGANISM: Artificial
<220> FEATURE:
<223> OTHER INFORMATION: COMPLEMENTARITY DETERMINING REGION 2; can be
      chemically synthesized

<400> SEQUENCE: 24

Ser Ile Ser Gly Ser Gly Ser Asp Thr Leu Tyr Ala Asp Ser Val Lys
1               5                   10                  15

Gly

<210> SEQ ID NO 25
<211> LENGTH: 17
<212> TYPE: PRT
<213> ORGANISM: Artificial
<220> FEATURE:
<223> OTHER INFORMATION: COMPLEMENTARITY DETERMINING REGION 2; can be
      chemically synthesized

<400> SEQUENCE: 25

Ser Ile Asn Gly Arg Gly Asp Asp Thr Arg Tyr Ala Asp Ser Val Lys
1               5                   10                  15

Gly

<210> SEQ ID NO 26
<211> LENGTH: 17
<212> TYPE: PRT
<213> ORGANISM: Artificial
<220> FEATURE:
<223> OTHER INFORMATION: COMPLEMENTARITY DETERMINING REGION 2; can be
      chemically synthesized

<400> SEQUENCE: 26

Ala Ile Ser Ala Asp Ser Ser Thr Lys Asn Tyr Ala Asp Ser Val Lys
1               5                   10                  15

Gly

<210> SEQ ID NO 27
<211> LENGTH: 17
<212> TYPE: PRT
<213> ORGANISM: Artificial
<220> FEATURE:
<223> OTHER INFORMATION: COMPLEMENTARITY DETERMINING REGION 2; can be
      chemically synthesized

<400> SEQUENCE: 27

Ala Ile Ser Ala Asp Ser Ser Asp Lys Arg Tyr Ala Asp Ser Val Lys
```

```
1               5                   10                  15
Gly

<210> SEQ ID NO 28
<211> LENGTH: 18
<212> TYPE: PRT
<213> ORGANISM: Artificial
<220> FEATURE:
<223> OTHER INFORMATION: COMPLEMENTARITY DETERMINING REGION 2; can be
      chemically synthesized

<400> SEQUENCE: 28

Arg Asp Ile Ser Thr Gly Gly Gly Tyr Ser Tyr Ala Asp Ser Val
1               5                   10                  15

Lys Gly

<210> SEQ ID NO 29
<211> LENGTH: 32
<212> TYPE: PRT
<213> ORGANISM: Artificial
<220> FEATURE:
<223> OTHER INFORMATION: FRAMEWORK REGION 3; can be chemically
      synthesized

<400> SEQUENCE: 29

Arg Phe Thr Ile Ser Met Asp Tyr Thr Lys Gln Thr Val Tyr Leu His
1               5                   10                  15

Met Asn Ser Leu Arg Pro Glu Asp Thr Gly Leu Tyr Tyr Cys Lys Ile
                20                  25                  30

<210> SEQ ID NO 30
<211> LENGTH: 32
<212> TYPE: PRT
<213> ORGANISM: Artificial
<220> FEATURE:
<223> OTHER INFORMATION: FRAMEWORK REGION 3; can be chemically
      synthesized

<400> SEQUENCE: 30

Arg Phe Thr Ile Ser Arg Asp Tyr Asp Lys Asn Thr Leu Tyr Leu Gln
1               5                   10                  15

Met Asn Ser Leu Arg Pro Glu Asp Thr Gly Leu Tyr Tyr Cys Lys Ile
                20                  25                  30

<210> SEQ ID NO 31
<211> LENGTH: 32
<212> TYPE: PRT
<213> ORGANISM: Artificial
<220> FEATURE:
<223> OTHER INFORMATION: FRAMEWORK REGION 3; can be chemically
      synthesized

<400> SEQUENCE: 31

Arg Phe Thr Ile Ser Arg Asp Asn Ala Lys Thr Thr Leu Tyr Leu Gln
1               5                   10                  15

Met Asn Ser Leu Lys Pro Glu Asp Thr Ala Val Tyr Tyr Cys Thr Ile
                20                  25                  30

<210> SEQ ID NO 32
<211> LENGTH: 32
<212> TYPE: PRT
<213> ORGANISM: Artificial
<220> FEATURE:
<223> OTHER INFORMATION: FRAMEWORK REGION 3; can be chemically
      synthesized
```

-continued

```
<400> SEQUENCE: 32

Arg Phe Ser Ile Ser Arg Asp Asn Ala Lys Asn Thr Leu Tyr Leu Gln
1               5                   10                  15

Met Asn Ser Leu Lys Pro Glu Asp Thr Ala Glu Tyr Tyr Cys Thr Ile
            20                  25                  30

<210> SEQ ID NO 33
<211> LENGTH: 32
<212> TYPE: PRT
<213> ORGANISM: Artificial
<220> FEATURE:
<223> OTHER INFORMATION: FRAMEWORK REGION 3; can be chemically
      synthesized

<400> SEQUENCE: 33

Arg Phe Thr Ile Ser Arg Asp Asn Ala Lys Lys Met Leu Tyr Leu Glu
1               5                   10                  15

Met Asn Ser Leu Lys Pro Glu Asp Thr Ala Val Tyr Tyr Cys Val Ile
            20                  25                  30

<210> SEQ ID NO 34
<211> LENGTH: 32
<212> TYPE: PRT
<213> ORGANISM: Artificial
<220> FEATURE:
<223> OTHER INFORMATION: FRAMEWORK REGION 3; can be chemically
      synthesized

<400> SEQUENCE: 34

Arg Phe Thr Ile Ser Arg Asp Asn Ala Lys Lys Met Leu Tyr Leu Glu
1               5                   10                  15

Met Asn Ser Leu Lys Ser Glu Asp Thr Ala Val Tyr Tyr Cys Val Ile
            20                  25                  30

<210> SEQ ID NO 35
<211> LENGTH: 32
<212> TYPE: PRT
<213> ORGANISM: Artificial
<220> FEATURE:
<223> OTHER INFORMATION: FRAMEWORK REGION 3; can be chemically
      synthesized

<400> SEQUENCE: 35

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Leu Tyr Tyr Cys Ala Lys
            20                  25                  30

<210> SEQ ID NO 36
<211> LENGTH: 8
<212> TYPE: PRT
<213> ORGANISM: Artificial
<220> FEATURE:
<223> OTHER INFORMATION: COMPLEMENTARITY DETERMINING REGION 3; can be
      chemically synthesized

<400> SEQUENCE: 36

Arg Arg Thr Trp His Ser Glu Leu
1               5

<210> SEQ ID NO 37
<211> LENGTH: 8
<212> TYPE: PRT
<213> ORGANISM: Artificial
<220> FEATURE:
<223> OTHER INFORMATION: COMPLEMENTARITY DETERMINING REGION 3; can be
```

```
                chemically synthesized

<400> SEQUENCE: 37

Arg Arg Thr Trp His Ser Glu Leu
1               5

<210> SEQ ID NO 38
<211> LENGTH: 6
<212> TYPE: PRT
<213> ORGANISM: Artificial
<220> FEATURE:
<223> OTHER INFORMATION: COMPLEMENTARITY DETERMINING REGION 3; can be
      chemically synthesized

<400> SEQUENCE: 38

Gly Gly Ser Leu Ser Arg
1               5

<210> SEQ ID NO 39
<211> LENGTH: 7
<212> TYPE: PRT
<213> ORGANISM: Artificial
<220> FEATURE:
<223> OTHER INFORMATION: COMPLEMENTARITY DETERMINING REGION 3; can be
      chemically synthesized

<400> SEQUENCE: 39

Gly Arg Ser Val Ser Arg Ser
1               5

<210> SEQ ID NO 40
<211> LENGTH: 5
<212> TYPE: PRT
<213> ORGANISM: Artificial
<220> FEATURE:
<223> OTHER INFORMATION: COMPLEMENTARITY DETERMINING REGION 3; can be
      chemically synthesized

<400> SEQUENCE: 40

Gly Arg Gly Ser Pro
1               5

<210> SEQ ID NO 41
<211> LENGTH: 5
<212> TYPE: PRT
<213> ORGANISM: Artificial
<220> FEATURE:
<223> OTHER INFORMATION: COMPLEMENTARITY DETERMINING REGION 3; can be
      chemically synthesized

<400> SEQUENCE: 41

Gly Arg Gly Ser Pro
1               5

<210> SEQ ID NO 42
<211> LENGTH: 13
<212> TYPE: PRT
<213> ORGANISM: Artificial
<220> FEATURE:
<223> OTHER INFORMATION: COMPLEMENTARITY DETERMINING REGION 3; can be
      chemically synthesized

<400> SEQUENCE: 42

Asp Arg Glu Ala Gln Val Asp Thr Leu Asp Phe Asp Tyr
1               5                   10

<210> SEQ ID NO 43
<211> LENGTH: 11
```

```
<212> TYPE: PRT
<213> ORGANISM: Artificial
<220> FEATURE:
<223> OTHER INFORMATION: FRAMEWORK REGION 4; can be chemically
      synthesized

<400> SEQUENCE: 43

Trp Gly Gln Gly Thr Gln Val Thr Val Ser Ser
1               5                   10

<210> SEQ ID NO 44
<211> LENGTH: 11
<212> TYPE: PRT
<213> ORGANISM: Artificial
<220> FEATURE:
<223> OTHER INFORMATION: FRAMEWORK REGION 4; can be chemically
      synthesized

<400> SEQUENCE: 44

Trp Gly Gln Gly Thr Gln Val Thr Val Ser Ser
1               5                   10

<210> SEQ ID NO 45
<211> LENGTH: 11
<212> TYPE: PRT
<213> ORGANISM: Artificial
<220> FEATURE:
<223> OTHER INFORMATION: FRAMEWORK REGION 4; can be chemically
      synthesized

<400> SEQUENCE: 45

Ser Ser Gln Gly Thr Gln Val Thr Val Ser Ser
1               5                   10

<210> SEQ ID NO 46
<211> LENGTH: 11
<212> TYPE: PRT
<213> ORGANISM: Artificial
<220> FEATURE:
<223> OTHER INFORMATION: FRAMEWORK REGION 4; can be chemically
      synthesized

<400> SEQUENCE: 46

Arg Thr Gln Gly Thr Gln Val Thr Val Ser Ser
1               5                   10

<210> SEQ ID NO 47
<211> LENGTH: 11
<212> TYPE: PRT
<213> ORGANISM: Artificial
<220> FEATURE:
<223> OTHER INFORMATION: FRAMEWORK REGION 4; can be chemically
      synthesized

<400> SEQUENCE: 47

Ser Ser Pro Gly Thr Gln Val Thr Val Ser Ser
1               5                   10

<210> SEQ ID NO 48
<211> LENGTH: 11
<212> TYPE: PRT
<213> ORGANISM: Artificial
<220> FEATURE:
<223> OTHER INFORMATION: FRAMEWORK REGION 4; can be chemically
      synthesized

<400> SEQUENCE: 48

Ala Ser Gln Gly Thr Gln Val Thr Val Ser Ser
1               5                   10
```

<210> SEQ ID NO 49
<211> LENGTH: 11
<212> TYPE: PRT
<213> ORGANISM: Artificial
<220> FEATURE:
<223> OTHER INFORMATION: FRAMEWORK REGION 4; can be chemically
      synthesized

<400> SEQUENCE: 49

Arg Gly Gln Gly Thr Gln Val Thr Val Ser Ser
1               5                   10

<210> SEQ ID NO 50
<211> LENGTH: 117
<212> TYPE: PRT
<213> ORGANISM: Artificial
<220> FEATURE:
<223> OTHER INFORMATION: Nanobody sequence; can be chemically
      synthesized

<400> SEQUENCE: 50

Ala Val Gln Leu Val Glu Ser Gly Gly Gly Leu Val Gln Gly Gly Gly
1               5                   10                  15

Ser Leu Arg Leu Ala Cys Ala Ala Ser Glu Arg Ile Phe Asp Leu Asn
            20                  25                  30

Leu Met Gly Trp Tyr Arg Gln Gly Pro Gly Asn Glu Arg Glu Leu Val
        35                  40                  45

Ala Thr Cys Ile Thr Val Gly Asp Ser Thr Asn Tyr Ala Asp Ser Val
    50                  55                  60

Lys Gly Arg Phe Thr Ile Ser Met Asp Tyr Thr Lys Gln Thr Val Tyr
65                  70                  75                  80

Leu His Met Asn Ser Leu Arg Pro Glu Asp Thr Gly Leu Tyr Tyr Cys
                85                  90                  95

Lys Ile Arg Arg Thr Trp His Ser Glu Leu Trp Gly Gly Thr Gln
            100                 105                 110

Val Thr Val Ser Ser
        115

<210> SEQ ID NO 51
<211> LENGTH: 116
<212> TYPE: PRT
<213> ORGANISM: Artificial
<220> FEATURE:
<223> OTHER INFORMATION: Nanobody sequence; can be chemically
      synthesized

<400> SEQUENCE: 51

Glu Val Gln Leu Val Glu Ser Gly Gly Gly Leu Val Glu Gly Gly Gly
1               5                   10                  15

Ser Leu Arg Leu Ala Cys Ala Ala Ser Glu Arg Ile Trp Asp Ile Asn
            20                  25                  30

Leu Leu Gly Trp Tyr Arg Gln Gly Pro Gly Asn Glu Arg Glu Leu Val
        35                  40                  45

Ala Thr Ile Thr Val Gly Asp Ser Thr Ser Tyr Ala Asp Ser Val Lys
    50                  55                  60

Gly Arg Phe Thr Ile Ser Arg Asp Tyr Asp Lys Asn Thr Leu Tyr Leu
65                  70                  75                  80

Gln Met Asn Ser Leu Arg Pro Glu Asp Thr Gly Leu Tyr Tyr Cys Lys
                85                  90                  95

Ile Arg Arg Thr Trp His Ser Glu Leu Trp Gly Gln Gly Thr Gln Val 100                 105                 110

Thr Val Ser Ser
        115

<210> SEQ ID NO 52
<211> LENGTH: 115
<212> TYPE: PRT
<213> ORGANISM: Artificial
<220> FEATURE:
<223> OTHER INFORMATION: Nanobody sequence; can be chemically
      synthesized

<400> SEQUENCE: 52

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 53
<211> LENGTH: 116
<212> TYPE: PRT
<213> ORGANISM: Artificial
<220> FEATURE:
<223> OTHER INFORMATION: Nanobody sequence; can be chemically
      synthesized

<400> SEQUENCE: 53

Ala Val Gln Leu Val Asp Ser Gly Gly Gly Leu Val Gln Pro Gly Gly
1               5                   10                  15

Ser Leu Arg Leu Ser Cys Ala Ala Ser Gly Phe Ser Phe Gly Ser Phe
            20                  25                  30

Gly Met Ser Trp Val Arg Gln Tyr Pro Gly Lys Glu Pro Glu Trp Val
        35                  40                  45

Ser Ser Ile Asn Gly Arg Gly Asp Asp Thr Arg Tyr Ala Asp Ser Val
    50                  55                  60

Lys Gly Arg Phe Ser Ile Ser Arg Asp Asn Ala Lys Asn Thr Leu Tyr
65                  70                  75                  80

Leu Gln Met Asn Ser Leu Lys Pro Glu Asp Thr Ala Glu Tyr Tyr Cys
                85                  90                  95

Thr Ile Gly Arg Ser Val Ser Arg Ser Arg Thr Gln Gly Thr Gln Val
            100                 105                 110

Thr Val Ser Ser
        115

<210> SEQ ID NO 54
<211> LENGTH: 114
<212> TYPE: PRT
<213> ORGANISM: Artificial

-continued

```
<220> FEATURE:
<223> OTHER INFORMATION: Nanobody sequence; can be chemically
      synthesized

<400> SEQUENCE: 54

Ala Val Gln Leu Val Glu Ser Gly Gly Leu Val Gln Pro Gly Gly
1               5                   10                  15

Ser Leu Arg Leu Thr Cys Thr Ala Ser Gly Phe Thr Phe Arg Ser Phe
            20                  25                  30

Gly Met Ser Trp Val Arg Gln Ala Pro Gly Lys Asp Gln Glu Trp Val
        35                  40                  45

Ser Ala Ile Ser Ala Asp Ser Ser Thr Lys Asn Tyr Ala Asp Ser Val
    50                  55                  60

Lys Gly Arg Phe Thr Ile Ser Arg Asp Asn Ala Lys Lys Met Leu Tyr
65                  70                  75                  80

Leu Glu Met Asn Ser Leu Lys Pro Glu Asp Thr Ala Val Tyr Tyr Cys
                85                  90                  95

Val Ile Gly Arg Gly Ser Pro Ser Pro Gly Thr Gln Val Thr Val
            100                 105                 110

Ser Ser

<210> SEQ ID NO 55
<211> LENGTH: 114
<212> TYPE: PRT
<213> ORGANISM: Artificial
<220> FEATURE:
<223> OTHER INFORMATION: Nanobody sequence; can be chemically
      synthesized

<400> SEQUENCE: 55

Gln Val Gln Leu Ala Glu Ser Gly Gly Gly Leu Val Gln Pro Gly Gly
1               5                   10                  15

Ser Leu Arg Leu Thr Cys Thr Ala Ser Gly Phe Thr Phe Gly Ser Phe
            20                  25                  30

Gly Met Ser Trp Val Arg Gln Ala Pro Gly Glu Gly Leu Glu Trp Val
        35                  40                  45

Ser Ala Ile Ser Ala Asp Ser Ser Asp Lys Arg Tyr Ala Asp Ser Val
    50                  55                  60

Lys Gly Arg Phe Thr Ile Ser Arg Asp Asn Ala Lys Lys Met Leu Tyr
65                  70                  75                  80

Leu Glu Met Asn Ser Leu Lys Ser Glu Asp Thr Ala Val Tyr Tyr Cys
                85                  90                  95

Val Ile Gly Arg Gly Ser Pro Ala Ser Gln Gly Thr Gln Val Thr Val
            100                 105                 110

Ser Ser

<210> SEQ ID NO 56
<211> LENGTH: 123
<212> TYPE: PRT
<213> ORGANISM: Artificial
<220> FEATURE:
<223> OTHER INFORMATION: Nanobody sequence; can be chemically
      synthesized

<400> SEQUENCE: 56

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Trp Met Tyr Trp Val Arg Val Ala Pro Gly Lys Gly Leu Glu Arg Ile
         35                  40                  45

Ser Arg Asp Ile Ser Thr Gly Gly Tyr Ser Tyr Tyr Ala Asp Ser
 50                      55                  60

Val Lys Gly Arg Phe Thr Ile Ser Arg Asp Asn Ala Lys Asn Thr Leu
 65                  70                  75                  80

Tyr Leu Gln Met Asn Ser Leu Lys Pro Glu Asp Thr Ala Leu Tyr Tyr
                 85                  90                  95

Cys Ala Lys Asp Arg Glu Ala Gln Val Asp Thr Leu Asp Phe Asp Tyr
             100                 105                 110

Arg Gly Gln Gly Thr Gln Val Thr Val Ser Ser
         115                 120
```

<210> SEQ ID NO 57
<211> LENGTH: 115
<212> TYPE: PRT
<213> ORGANISM: Artificial
<220> FEATURE:
<223> OTHER INFORMATION: Nanobody sequence; can be chemically
      synthesized

<400> SEQUENCE: 57

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Arg Ser Phe
             20                  25                  30

Gly Met Ser Trp Val Arg Gln Ala Pro Gly Lys Glu Pro Glu Trp Val
         35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Lys Pro Glu Asp Thr Ala Val Tyr Tyr Cys
             85                  90                  95

Thr Ile Gly Gly Ser Leu Ser Arg Ser Ser Gln Gly Thr Gln Val Thr
             100                 105                 110

Val Ser Ser
        115
```

<210> SEQ ID NO 58
<211> LENGTH: 115
<212> TYPE: PRT
<213> ORGANISM: Artificial
<220> FEATURE:
<223> OTHER INFORMATION: Nanobody sequence; can be chemically
      synthesized

<400> SEQUENCE: 58

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Glu Pro Glu Trp Val
         35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80
```

```
Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 59
<211> LENGTH: 115
<212> TYPE: PRT
<213> ORGANISM: Artificial
<220> FEATURE:
<223> OTHER INFORMATION: Nanobody sequence; can be chemically
      synthesized

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 60
<211> LENGTH: 115
<212> TYPE: PRT
<213> ORGANISM: Artificial
<220> FEATURE:
<223> OTHER INFORMATION: Nanobody sequence; can be chemically
      synthesized

<400> SEQUENCE: 60

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

```
<210> SEQ ID NO 61
<211> LENGTH: 115
<212> TYPE: PRT
<213> ORGANISM: Artificial
<220> FEATURE:
<223> OTHER INFORMATION: Nanobody sequence; can be chemically
      synthesized

<400> SEQUENCE: 61

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 62
<211> LENGTH: 115
<212> TYPE: PRT
<213> ORGANISM: Artificial
<220> FEATURE:
<223> OTHER INFORMATION: Nanobody sequence; can be chemically
      synthesized

<400> SEQUENCE: 62

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 63
<211> LENGTH: 115
<212> TYPE: PRT
<213> ORGANISM: Artificial
<220> FEATURE:
<223> OTHER INFORMATION: Nanobody sequence; can be chemically
      synthesized
```

<400> SEQUENCE: 63

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 64
<211> LENGTH: 115
<212> TYPE: PRT
<213> ORGANISM: Artificial
<220> FEATURE:
<223> OTHER INFORMATION: Nanobody sequence; can be chemically
      synthesized

<400> SEQUENCE: 64

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 65
<211> LENGTH: 6
<212> TYPE: PRT
<213> ORGANISM: Artificial
<220> FEATURE:
<223> OTHER INFORMATION: COMPLEMENTARITY DETERMINING REGION 3; can be
      chemically synthesized

<400> SEQUENCE: 65

Ser Pro Ser Gly Phe Asn
1               5